United States Patent
Hu et al.

(10) Patent No.: US 10,514,373 B2
(45) Date of Patent: Dec. 24, 2019

(54) PLUS-FRACTION CORRECTIONS FOR HEAVY HYDROCARBON LIQUIDS

(71) Applicant: Stratum Reservoir (Canada), ULC, Calgary (CA)

(72) Inventors: YunFeng Hu, Calgary (CA); F. Brent Thomas, Crossfield (CA)

(73) Assignee: STRATUM RESERVOIR (CANADA), ULC, Calgary (CA)

( * ) Notice: Subject to any disclaimer, the term of this patent is extended or adjusted under 35 U.S.C. 154(b) by 1296 days.

(21) Appl. No.: 14/517,307

(22) Filed: Oct. 17, 2014

(65) Prior Publication Data

US 2015/0112609 A1 Apr. 23, 2015

(30) Foreign Application Priority Data

Oct. 18, 2013 (CA) ..................................... 2830384

(51) Int. Cl.
*G01N 33/28* (2006.01)
*G01N 30/86* (2006.01)
*G01N 30/00* (2006.01)
*G01N 30/88* (2006.01)

(52) U.S. Cl.
CPC ............. *G01N 33/28* (2013.01); *G01N 30/00* (2013.01); *G01N 30/8675* (2013.01); *G01N 2030/009* (2013.01); *G01N 2030/8854* (2013.01)

(58) Field of Classification Search
CPC .................................................... G01N 33/28
See application file for complete search history.

(56) References Cited

U.S. PATENT DOCUMENTS

| 9,458,389 B1* | 10/2016 | Schabron ............... G01N 33/28 |
| 9,458,715 B2* | 10/2016 | van Hal ................ E21B 49/087 |
| 2012/0085149 A1 | 4/2012 | Al-Eid et al. |
| 2015/0039241 A1* | 2/2015 | Moorwood ........... G06F 19/703 702/24 |

FOREIGN PATENT DOCUMENTS

| WO | 2009073269 A1 | 6/2009 |
| WO | 2013121204 A2 | 8/2013 |

OTHER PUBLICATIONS

European Patent Application No. 14189589, Office Action dated Nov. 21, 2016.

(Continued)

*Primary Examiner* — John E Breene
*Assistant Examiner* — Jeffrey C Morgan
(74) *Attorney, Agent, or Firm* — Winston & Strawn LLP (57) ABSTRACT

A method of determining the plus-fraction correction for a heavy oil sample including analyzing the heavy oil sample using gas chromatography, selecting an elution ratio based on the percentage of plus-fraction elution, applying the elution ratio to provide a maximum carbon number and a plus-fraction correction to compensate for the non-elution of the plus-fraction. An elution ratio as a function of the percentage of $C_{60+}$ elution is provided. A corrected molecular weight for the $C_{60+}$ fraction ($MW_{C60+}$) and the $C_{90+}$ fraction ($MW_{C90+}$) as well as the total oil (MW) is provided.

18 Claims, 6 Drawing Sheets

(56) References Cited

OTHER PUBLICATIONS

European Patent Application No. 14189589.6, Notice of Allowance dated Apr. 21, 2017.
Zuo, Julian Y., et al.—"Plus Fraction Characterization and PVT Data Regression for Reservoir Fluids near Critical Conditions," SPE 64520, paper prepared for presentation at the SPE Asia Pacific Oil and Gas Conference and Exhibition held in Brisbane, Australia, Oct. 16-18, 2000, 12 pages.
EPO Extended European Report dated Mar. 30, 2015, for European Patent Application No. 14189589.6.
EPO Extended European Report dated Mar. 10, 2015, for European Patent Application No. 14189589.6.
EPO Intention to Grant dated Jul. 18, 2016, for European Patent Application No. 14189589.6.

* cited by examiner

| AC60 | 79500 | | | | | | | | |
|---|---|---|---|---|---|---|---|---|---|
| AC60+ | 2544000 | | | | | | | | |
| Carbon Number | Molecular Weight | Area | Mass Fraction | Moles | Mole Fraction C60+ | MW C60+ | Mole Fraction C90+ | MW C90+ |
| CN | MW | | | | | | | |
| 60 | 843.62 | 79500 | 0.0313 | 3.70E-05 | 0.0406 | 34.2877 | | |
| 61 | 857.64 | 78238.095 | 0.0308 | 3.59E-05 | 0.0393 | 33.7434 | | |
| 62 | 871.67 | 76976.19 | 0.0303 | 3.47E-05 | 0.0381 | 33.1992 | | |
| 63 | 885.7 | 75714.285 | 0.0298 | 3.36E-05 | 0.0369 | 32.6549 | | |
| 64 | 899.72 | 74452.38 | 0.0293 | 3.25E-05 | 0.0357 | 32.1107 | | |
| 65 | 913.75 | 73190.475 | 0.0288 | 3.15E-05 | 0.0345 | 31.5664 | | |
| 66 | 927.78 | 71928.57 | 0.0283 | 3.05E-05 | 0.0334 | 31.0222 | | |
| 67 | 941.8 | 70666.665 | 0.0278 | 2.95E-05 | 0.0324 | 30.4779 | | |
| 68 | 955.83 | 69404.76 | 0.0273 | 2.85E-05 | 0.0313 | 29.9337 | | |
| 69 | 969.86 | 68142.855 | 0.0268 | 2.76E-05 | 0.0303 | 29.3894 | | |
| 70 | 983.88 | 66880.95 | 0.0263 | 2.67E-05 | 0.0293 | 28.8452 | | |
| 71 | 997.91 | 65619.045 | 0.0258 | 2.58E-05 | 0.0284 | 28.3009 | | |
| 72 | 1011.94 | 64357.14 | 0.0253 | 2.50E-05 | 0.0274 | 27.7567 | | |
| 73 | 1025.96 | 63095.235 | 0.0248 | 2.42E-05 | 0.0265 | 27.2124 | | |
| 74 | 1039.99 | 61833.33 | 0.0243 | 2.34E-05 | 0.0256 | 26.6682 | | |
| 75 | 1054.02 | 60571.425 | 0.0238 | 2.26E-05 | 0.0248 | 26.1239 | | |
| 76 | 1068.04 | 59309.52 | 0.0233 | 2.18E-05 | 0.024 | 25.5797 | | |
| 77 | 1082.07 | 58047.615 | 0.0228 | 2.11E-05 | 0.0231 | 25.0354 | | |
| 78 | 1096.1 | 56785.71 | 0.0223 | 2.04E-05 | 0.0223 | 24.4912 | | |
| 79 | 1110.12 | 55523.805 | 0.0218 | 1.97E-05 | 0.0216 | 23.9469 | | |

FIG.4A

| | | | | | | | |
|---|---|---|---|---|---|---|---|
| 80 | 1124.15 | 54261.9 | 0.0213 | 1.90E-05 | 0.0208 | 23.4027 | | |
| 81 | 1138.18 | 52999.995 | 0.0208 | 1.83E-05 | 0.0201 | 22.8584 | | |
| 82 | 1152.2 | 51738.09 | 0.0203 | 1.77E-05 | 0.0194 | 22.3142 | | |
| 83 | 1166.23 | 50476.185 | 0.0198 | 1.70E-05 | 0.0187 | 21.7699 | | |
| 84 | 1180.26 | 49214.28 | 0.0193 | 1.64E-05 | 0.018 | 21.2257 | | |
| 85 | 1194.28 | 47952.375 | 0.0188 | 1.58E-05 | 0.0173 | 20.6814 | | |
| 86 | 1208.31 | 46690.47 | 0.0184 | 1.52E-05 | 0.0167 | 20.1372 | | |
| 87 | 1222.34 | 45428.565 | 0.0179 | 1.46E-05 | 0.016 | 19.5929 | | |
| 88 | 1236.36 | 44166.66 | 0.0174 | 1.40E-05 | 0.0154 | 19.0487 | | |
| 89 | 1250.39 | 42904.755 | 0.0169 | 1.35E-05 | 0.0148 | 18.5044 | | |
| 90 | 1264.42 | 41642.85 | 0.0164 | 1.29E-05 | 0.0142 | 17.9602 | 0.0654 | 82.6879 |
| 91 | 1278.44 | 40380.945 | 0.0159 | 1.24E-05 | 0.0136 | 17.416 | 0.0627 | 80.1822 |
| 92 | 1292.47 | 39119.04 | 0.0154 | 1.19E-05 | 0.0131 | 16.8717 | 0.0601 | 77.6765 |
| 93 | 1306.5 | 37857.135 | 0.0149 | 1.14E-05 | 0.0125 | 16.3275 | 0.0575 | 75.1708 |
| 94 | 1320.52 | 36595.23 | 0.0144 | 1.09E-05 | 0.012 | 15.7832 | 0.055 | 72.6651 |
| 95 | 1334.55 | 35333.325 | 0.0139 | 1.04E-05 | 0.0114 | 15.239 | 0.0526 | 70.1594 |
| 96 | 1348.58 | 34071.42 | 0.0134 | 9.93E-06 | 0.0109 | 14.6947 | 0.0502 | 67.6537 |
| 97 | 1362.6 | 32809.515 | 0.0129 | 9.46E-06 | 0.0104 | 14.1505 | 0.0478 | 65.148 |
| 98 | 1376.63 | 31547.61 | 0.0124 | 9.01E-06 | 0.0099 | 13.6062 | 0.0455 | 62.6423 |
| 99 | 1390.66 | 30285.705 | 0.0119 | 8.56E-06 | 0.0094 | 13.062 | 0.0432 | 60.1366 |
| 100 | 1404.68 | 29023.8 | 0.0114 | 8.12E-06 | 0.0089 | 12.5177 | 0.041 | 57.6309 |
| 101 | 1418.71 | 27761.895 | 0.0109 | 7.69E-06 | 0.0084 | 11.9735 | 0.0389 | 55.1253 |
| 102 | 1432.74 | 26499.99 | 0.0104 | 7.27E-06 | 0.008 | 11.4292 | 0.0367 | 52.6196 |
| 103 | 1446.76 | 25238.085 | 0.0099 | 6.86E-06 | 0.0075 | 10.885 | 0.0346 | 50.1139 |

FIG.4B

| | | | | | | | | |
|---|---|---|---|---|---|---|---|---|
| 104 | 1460.79 | 23976.18 | 0.0094 | 6.45E-06 | 0.0071 | 10.3407 | 0.0326 | 47.6082 |
| 105 | 1474.82 | 22714.275 | 0.0089 | 6.05E-06 | 0.0066 | 9.7965 | 0.0306 | 45.1025 |
| 106 | 1488.84 | 21452.37 | 0.0084 | 5.66E-06 | 0.0062 | 9.2522 | 0.0286 | 42.5968 |
| 107 | 1502.87 | 20190.465 | 0.0079 | 5.28E-06 | 0.0058 | 8.708 | 0.0267 | 40.0911 |
| 108 | 1516.9 | 18928.56 | 0.0074 | 4.91E-06 | 0.0054 | 8.1637 | 0.0248 | 37.5854 |
| 109 | 1530.92 | 17666.655 | 0.0069 | 4.54E-06 | 0.005 | 7.6195 | 0.0229 | 35.0797 |
| 110 | 1544.95 | 16404.75 | 0.0064 | 4.17E-06 | 0.0046 | 7.0752 | 0.0211 | 32.574 |
| 111 | 1558.98 | 15142.845 | 0.006 | 3.82E-06 | 0.0042 | 6.531 | 0.0193 | 30.0683 |
| 112 | 1573 | 13880.94 | 0.0055 | 3.47E-06 | 0.0038 | 5.9867 | 0.0175 | 27.5626 |
| 113 | 1587.03 | 12619.035 | 0.005 | 3.13E-06 | 0.0034 | 5.4425 | 0.0158 | 25.0569 |
| 114 | 1601.06 | 11357.13 | 0.0045 | 2.79E-06 | 0.0031 | 4.8982 | 0.0141 | 22.5512 |
| 115 | 1615.08 | 10095.225 | 0.004 | 2.46E-06 | 0.0027 | 4.354 | 0.0124 | 20.0455 |
| 116 | 1629.11 | 8833.32 | 0.0035 | 2.13E-06 | 0.0023 | 3.8097 | 0.0108 | 17.5398 |
| 117 | 1643.14 | 7571.415 | 0.003 | 1.81E-06 | 0.002 | 3.2655 | 0.0091 | 15.0341 |
| 118 | 1657.16 | 6309.51 | 0.0025 | 1.50E-06 | 0.0016 | 2.7212 | 0.0076 | 12.5284 |
| 119 | 1671.19 | 5047.605 | 0.002 | 1.19E-06 | 0.0013 | 2.177 | 0.006 | 10.0227 |
| 120 | 1685.22 | 3785.7 | 0.0015 | 8.83E-07 | 0.001 | 1.6327 | 0.0045 | 7.5171 |
| 121 | 1699.24 | 2523.795 | 0.001 | 5.84E-07 | 0.0006 | 1.0885 | 0.0029 | 5.0114 |
| 122 | 1713.27 | 1261.89 | 0.0005 | 2.90E-07 | 0.0003 | 0.5442 | 0.0015 | 2.5057 |
| 123 | 1727.3 | 0.015 | 0 | 0.00E+00 | 0 | 0 | 0 | 0 |
| Summations | | 2544000 | 1 | 9.11E-04 | 1 | 1097.2 | 1 | 1405.69 |
| | | | Moles C60+ | 1.98E-04 | | MW C60+ | | MW C90+ |
| | | | Moles C90+ | | | | | |

FIG. 4C though a gas chromatograph or using results from a previous gas chromatograph run for the heavy oil.

In an embodiment disclosed, the elution ratio (R), is determined according to the formula $R=0.0493 \ln(A_{C60+}/A_{Etotal} \times 100)+1.1746$.

In an embodiment disclosed, the method further includes determining a slope of a non-elution line according to the formula slope=$(0-A_{C60})/(C_{MAX}-60)$, and determining at least one area fraction for a carbon number ($C_{Ni}$) according to the formula $A_{CNi}=A_{C60}+\text{slope} \times (C_{Ni}-60)$.

In an embodiment disclosed, the method further includes determining an area fraction $A_{CNi}$, for each carbon number ($C_{Ni}$) between $C_{60}$ and $C_{MAX}$.

In an embodiment disclosed, the method further includes determining a mole fraction for each carbon number ($C_{Ni}$) between $C_{60}$ and $C_{MAX}$.

In an embodiment disclosed, the method further includes summing the molecular weight fraction for each carbon number ($C_{Ni}$) between $C_{60}$ and $C_{MAX}$ to determine a $C_{60+}$ molecular weight ($MW_{C60+}$) of the heavy oil.

In an embodiment disclosed, the method further includes summing the molecular weight fraction for each carbon number ($C_{Ni}$) between $C_{90}$ and $C_{MAX}$ to determine a $C_{90+}$ molecular weight ($MW_{C90+}$) for the heavy oil.

In an embodiment disclosed, the method further includes summing the molecular weight fraction for each carbon number ($C_{Ni}$) between $C_{MIN}$ and $C_{MAX}$ to determine a molecular weight (MW) of the heavy oil.

In an embodiment disclosed, $C_{MIN}$ equals $C_3$.

In an embodiment disclosed, the method further includes determining a plus-fraction area, between $C_{60}$ and $C_{MAX}$, according to the formula $A_{C60+}=\int A_{CNi} * dC_N$.

In an embodiment disclosed, the method further includes determining a plus-fraction area, between $C_{60}$ and $C_{MAX}$, according to the formula $A_{C60+}=A_{C60} \times C_{Ni}+\text{slope}(C_{Ni}^2/2-60 \times C_{Ni})$.

In an embodiment disclosed, $A_{C60+}/A_{Etotal} \times 100$ is between 1 percent and 100 percent. In an embodiment disclosed, $A_{C60+}/A_{Etotal} \times 100$ is between 2 percent and 40 percent. In an embodiment disclosed, $A_{C60+}/A_{Etotal} \times 100$ is between 2 percent and 30 percent.

A computer or system having one or more processors may be utilized to make the calculations of the present disclosure. In an embodiment, a non-transitory computer-readable medium has computer-readable code embodied therein. The computer-readable code is executable by a processor to use an analysis of the heavy oil using gas chromatography to provide a highest detected carbon number ($C_{EMAX}$), a total eluted area ($A_{Etotal}$), and a $C_{60+}$ eluted area ($A_{EC60+}$), and selecting an elution ratio (R) to compensate for the non-elution of a plus-fraction of the heavy oil, automatically determining a corrected plus-fraction area ($A_{C60+}$) from the elution ratio (R) and the $C_{60+}$ eluted area ($A_{EC60+}$) according to the formula $A_{C60+}=A_{EC60+} \times R$, and determining a $C_{60}$ area ($A_{C60}$) and maximum carbon number ($C_{MAX}$) for the heavy oil according to the formulas $A_{EC60+}=0.50 \times (C_{EMAX}-60) \times A_{C60}$ and $A_{C60+}=0.50 \times (C_{MAX}-60) \times A_{C60}$.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

PLUS-FRACTION CORRECTIONS FOR HEAVY HYDROCARBON LIQUIDS

BACKGROUND

Field

The present disclosure relates generally to analysis of heavy oil. More particularly, the present disclosure relates to chromatography of heavy oil.

Description of the Related Art

Chromatography includes the analysis of a compound to determine the identification and relative amount of the components. A sample of the compound is heated in a chromatographic column and the components detected at a detector.

Standards exist for the analysis of petroleum fractions including, for example, ASTM International standards relating to test methods for boiling range distribution of petroleum fractions by gas chromatography.

The quantification of heavy oil compositions is challenging for several reasons, which may include oxidation, emulsions, or impurities such as basic sediment and water (BS&W), or contamination.

However, one of the more difficult problems to resolve is the degree of non-elution, meaning the portion of the heavy oil that is not eluted, and thus does not arrive at the detector but instead remains behind in the chromatographic column.

It is, therefore, desirable to provide a method for chromatography of heavy oils.

SUMMARY

The technique used for heavy oil characterization is based upon treatment of the heavy oil as two portions. A first portion includes components having a carbon number up to and including a full elution carbon number, and a second portion includes components having a carbon number greater than the full elution carbon number. In an embodiment disclosed the full elution carbon number is 60, and the first portion includes components having a carbon number up to and including $C_{60}$, and the second portion includes components having a carbon number $C_{60+}$. The first portion of the heavy oil may be characterized by typical means, for example gas chromatography. The second portion of the heavy oil may be characterized by the methods described herein. The characterization of the first portion and the second portion may be combined to provide a characterization for the total oil.

In an embodiment disclosed, a method for determining the area fraction of the heavy oil that is not eluted and, since area is proportional to mass in a flame ionization detector (FID), this technique provides the mass fraction non-eluted.

In a first aspect, the present disclosure provides a method of determining a plus-fraction correction for a heavy oil including obtaining an analysis of the heavy oil using gas chromatography to provide a highest detected carbon number ($C_{EMAX}$), a total eluted area ($A_{Etotal}$), and a $C_{60+}$ eluted area ($A_{EC60+}$), selecting an elution ratio (R) to compensate for the non-elution of a plus-fraction of the heavy oil, determining a corrected plus-fraction area ($A_{C60+}$) from the elution ratio (R) and the $C_{60+}$ eluted area ($A_{EC60+}$) according to the formula $A_{C60+}=A_{EC60+} \times R$, and determining a $C_{60}$ area ($A_{C60}$) and maximum carbon number ($C_{MAX}$) for the heavy oil according to the formulas $A_{EC60+}=0.50 \times (C_{EMAX}-60) \times A_{C60}$ and $A_{C60+}=0.50 \times (C_{MAX}-60) \times A_{C60}$. The analysis of the heavy oil using gas chromatography may, for example, include running a sample of the heavy oil thorough a gas

DETAILED DESCRIPTION

Generally, the present disclosure provides a method for quantification of heavy oil which compensates for the non-elution of a portion of the heavy oil being tested.

Chromatography

Figure 1:
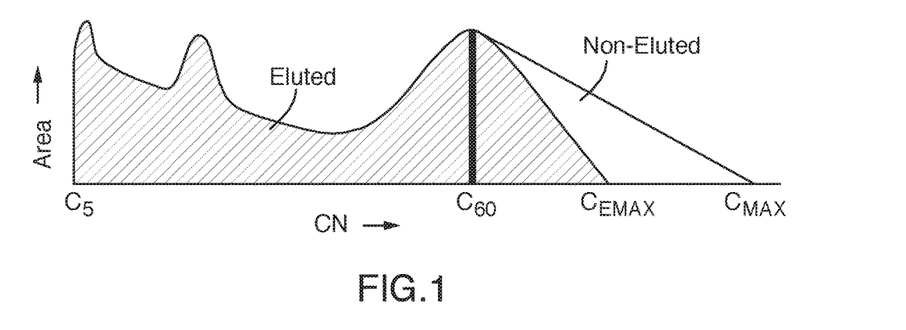
FIG. 1 is a sample chromatogram for a heavy oil sample.

Referring to FIG. 1, chromatography provides identification and quantification of the components of a compound, for example carbon atoms in heavy oil. The relative amount of each component, for example $C_{MIN}$ through $C_{EMAX}$ is indicated by the area of each component. The $C_{MIN}$ compound being the compound with the lowest carbon number eluted that registers a non-zero amount on the chromatograph. $C_{MIN}$ may be typically about $C_5$, as shown in FIG. 1 for a heavy oil at atmospheric conditions. The compound $C_{EMAX}$ being the compound with the highest carbon number eluted that registers a non-zero amount on the chromatograph. Components undoubtedly exist beyond $C_{EMAX}$, for example up to and including $C_{MAX}$, but are not eluted and therefore are not revealed by the chromatograph.

On the basis of poly-wax quantitative sample containing 16 components up to $C_{60}$, it is understood that using a high temperature gas chromatograph which operates up to 400° C. and uses helium as a carrier gas, that 100 percent elution is achieved at least up to and including $C_{60}$.

However, non-elution may start at $C_{61}$ or beyond but no quantitative sample exists where the degree of elution can be quantified. Therefore, in an embodiment disclosed, the full elution carbon number, being the highest carbon number where substantially one-hundred (100) percent elution is known to be achieved, is selected as $C_{60}$.

Elution Ratio R

In an embodiment disclosed, a method for determining the area fraction of the heavy oil non-eluted is provided, and since area is proportional to mass in a flame ionization detector (FID), this technique provides the mass fraction non-eluted.

In an embodiment disclosed, a non-eluted correction may be expressed as:

$$A_{NEC60+} = A_{EC60+}(R-1) \qquad \text{Eq. (1)}$$

In Eq. (1), $A_{NEC60+}$ is the area of the $C_{60+}$ not eluted and $A_{EC60+}$ is the area of the eluted $C_{60+}$. The elution ratio, R is equal to the total amount of hydrocarbons ($A_{EC60+}$ plus $A_{NEC60+}$) over the amount of hydrocarbons eluted ($A_{EC60+}$):

$$R = (A_{EC60+} + A_{NEC60+})/A_{EC60+} \qquad \text{Eq. (2)}$$

Eq. (2) may be rewritten by substituting the total area $A_{C60+}$ for the area eluted $A_{EC60+}$ plus the area non-eluted $A_{NEC60+}$:

$$R = A_{C60+}/A_{EC60+} \qquad \text{Eq. (3)}$$

The elution ratio, R, may be represented as:

$$R = C_{60+}\text{Total}/C_{60+}\text{Eluted} \qquad \text{Eq. (4)}$$

Determination of Elution Ratio, R

The $C_{60+}$ total area was derived from multiple blank runs performed after a sample of heavy oil was provided into the gas chromatograph column. The total area of the blanks cumulated and added to the eluted $C_{60+}$ area divided by the eluted $C_{60+}$ provides an elution ratio, R.

As an example, a heavy oil of known composition, labeled C-E006 was sampled in the gas chromatograph. This sample indicated an eluted $C_{60+}$ of 3.69569, but was known to have a total $C_{60+}$ of 5.3272, so a non-eluted $C_{60+}$ of 1.6315 may be determined. Applying Eq. (4) provides R=1.441.

In an embodiment disclosed, a correlation is provided to determine and use the elution ratio, R for a sample heavy oil of unknown composition.

Figure 2:
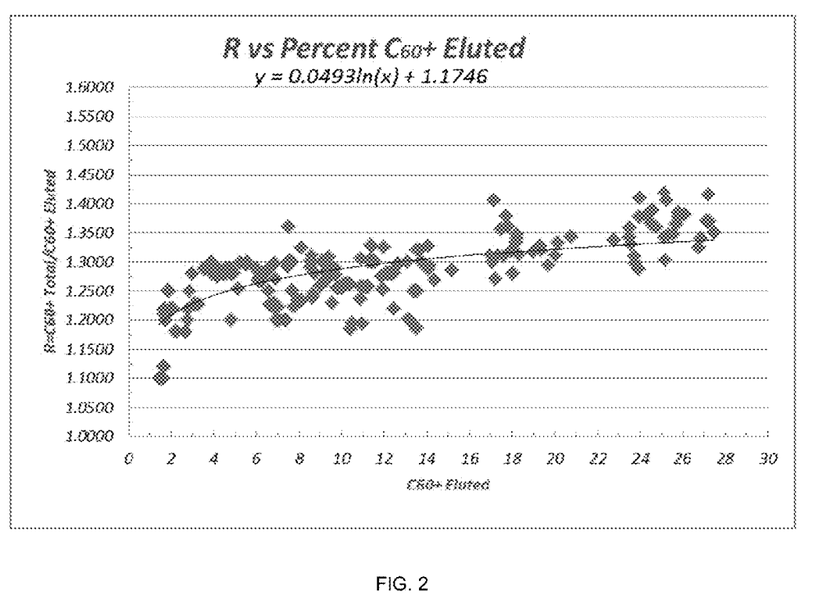
FIG. 2 is a correlation of an elution ratio R versus percent $C_{60+}$ eluted.

Referring to FIG. 2, the elution ratio, R is shown in correlation with percent $C_{60+}$ eluted for wide variety of heavy oils, that is percent $C_{60+}$ eluted=$A_{EC60+}/A_{Etotal} \times 100$. In an embodiment disclosed, the logarithmic curve fit correlation is represented as:

$$R = 0.0493 \ln(\text{percent } C_{60+} \text{ Eluted}) + 1.1746 \qquad \text{Eq. (5)}$$

A lower limit of 0.03 percent $C_{60+}$ may be used, in order to limit the R to 1.00, i.e., using Eq. (5) 0.0493 ln (0.03)+1.1746 equals substantially 1.00.

With a sample of heavy oil of unknown composition, one can conduct a gas chromatograph run, and using the percent $C_{60+}$ eluted ($A_{EC60}/A_{Etotal}*100$), determine the elution ratio, R, for the sample. The elution ratio, R determined in this manner may be used to compensate for the non-elution.

Figure 3:
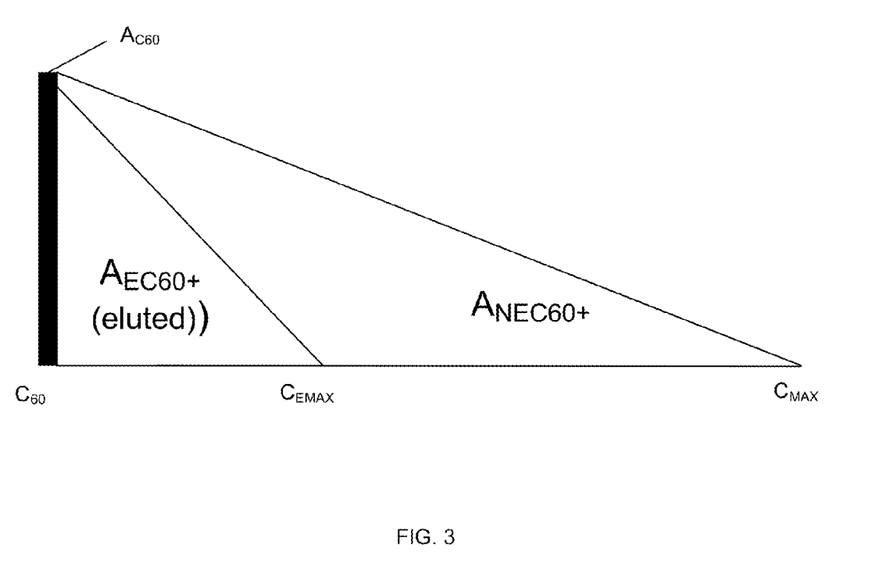
FIG. 3 is a detail of the $C_{60+}$ portion of FIG. 1, illustrating the relationship between an area eluted for $C_{60+}$ ($A_{EC60+}$) and an area non-eluted for $C_{60+}$ ($A_{NEC60+}$)

Referring to FIG. 3, a detail of the chromatograph of FIG. 1, from $C_{60}$ and higher is shown.

With the elution ratio, R and utilizing a linear elution phenomenon in the range of the components in question, $C_{60}$ through $C_{EMAX}$ and $C_{60}$ through and $C_{MAX}$, two linear equations result, where the area of the $C_{60}$ component is determined and subsequently the maximum carbon number (CN) of the non-eluted fraction is determined.

$A_{C60}$

Using the $A_{EC60+}$ value and $C_{EMAX}$ value measured from the heavy oil sample using the gas chromatograph, the area for the $C_{60}$ component, being $A_{C60}$, may be determined from:

$$A_{EC60+} = 0.50 \times (C_{EMAX} - 60) \times A_{C60} \qquad \text{Eq. (6)}$$

$C_{MAX}$

Then $A_{C60+}$ may be determined using R and $A_{EC60+}$ using Eq. 3, from above. Finally, $C_{MAX}$ may be calculated using the $A_{C60+}$ and $A_{C60}$ values from above, and equation (7) the maximum carbon number (CN) $C_{MAX}$ of the non-eluted fraction:

$$A_{C60+} = 0.50 \times (C_{MAX} - 60) \times A_{C60} \qquad \text{Eq. (7)}$$

Components

The equation of the gas chromatograph area for each component, including eluted and non-eluted contributions, may be derived, and from that the total area of the $C_{60+}$ may be determined.

Knowing the mass fraction for every component in the $C_{60+}$ range, and assuming a molecular weight (MW) increment of 14.0267 per carbon number (C—$H_2$), as in an alkane $C_nH_{2n+2}$, the renormalized $C_{60+}$ can be used to compute the $C_{60+}$ molecular weight.

The total $A_{C60+}$ is determined by integrating the area over the range of carbon numbers in the range.

Example 1: Heavy Oil Sample WL1

Referring to FIGS. 1, and 3, in an example, a heavy oil sample WL1 is analyzed using a high temperature gas chromatograph column, which operates at up to 400° C. and uses helium as a carrier gas. The full elution carbon number is selected as 60, that is, $C_{60}$.

The gas chromatograph indicates the presence of hydrocarbons up to $C_{108}$. That is, the highest degree carbon component showing any significant degree of detected elution is $C_{108}$. Therefore $C_{EMAX}=108$. The chromatograph further indicates that the $A_{EC60+}=1,908,000$ (area for eluted $C_{60+}$) and that $A_{Etotal}=14,290,000$ (total area).

Elution Ratio, R

In an embodiment, disclosed is a correlation between the elution ratio R, and the eluted $C_{60+}$ area $A_{EC60+}$ relative to the eluted total area $A_{Etotal}$. In this example, $A_{EC60+}/A_{Etotal}=1,908,000/14,290,000=0.1335=13.35$ percent.

Referring to FIG. 2, or Eq. (5), 13.35 percent provides an elution ratio, R of $=0.0493$ In $(13.35)+1.1746=1.3024$.

Using the $A_{EC60+}$ of 1,908,000 measured from the gas chromatograph and the elution ratio R=1.3024, $A_{C60+}$ is determined according to Eq. (3), which may be rearranged:

$$A_{C60+}=A_{EC60+} \times R \qquad \text{Eq. (8)}$$

Solving this equation provides $A_{C60+}=1,908,000 \times 1.3024=2,484,979$, which as above, is the total area of eluted and non-eluted for $C_{60+}$.

Quantification

Using Eq. (6) above with the $A_{EC60+}$ and $C_{EMAX}$ data from the chromatograph provides the area of the $C_{60}$ component:

$$1,908,000=0.50 \times (108-60) \times A_{C60} \qquad \text{from Eq. (6)}$$

In this example, with $A_{EC60+}=1,908,000$ and $C_{EMAX}=108$ from the chromatograph, Eq. (6) provides $A_{C60}=79,500.0$.

$C_{MAX}$ is determined according to Eq. (7) above using $A_{C60+}$ from Eq. (8):

$$2,484,979=0.50 \times (C_{MAX}-60) \times 79,500 \qquad \text{from Eq. (7)}$$

Solving Eq. (7) with $A_{C60}=2,484,979$ (this is the $A_{C60+}$ based on the elution ratio, R) and $A_{C60}=79,500.0$, provides $C_{MAX}=122.52$. As the carbon number (CN) must be an integer, $C_{MAX}$ is rounded up to the next higher integer. The calculated $C_{MAX}=122.52$ is thus rounded up to $C_{MAX}=123$.

Corrected Profile

Referring to FIG. 3, the slope of the non-eluted line is:

$$\text{Slope}=(0-A_{C60})/(C_{MAX}-60) \qquad \text{Eq. (9)}$$

As the values for $A_{C60}$, $C_{MAX}$, and $C_{EMAX}$ are known, Eq. (9) can be solved:

$$\text{Slope}=(0-79500.0)/(123-60)=-1261.9048 \qquad \text{from Eq. (9)}$$

The slope may then be used to determine the actual area for any component from $C_{60}$ through $C_{MAX}$, which takes into account the elution ratio, R, and thus compensates for the non-elution of the heavy oil:

$$A_{CNi}=A_{C60}+\text{Slope} \times (C_{Ni}-60) \qquad \text{Eq. (10)}$$

$$A_{CNi}=79,500-1,261.9048 \times (C_{Ni}-60) \qquad \text{from Eq. (10)}$$

For example, the area $A_{C100}$ for $C_{100}$ equals, according to Eq. (7):

$$79,500-1,261.9048 \times (100-60)=29,023.8 \qquad \text{from Eq. (10)}$$

This may be calculated between 0 to $C_{MAX}$). The equation of the gas chromatograph area for each component, including eluted and non-eluted contributions, is derived from which the total area of the $C_{60+}$ is readily available. This calculation can be performed for any of CNi, where in this case i is between 60 and $C_{MAX}$ (in this example $C_{MAX}=123$) to provide the area, and thus mass fraction, or mole fraction, or both for any component.

Mass Fraction (MF)

One can also sum, totalize, or integrate the area $A_{CNi}$ from $C_{60}$ to $C_{MAX}$, to determine the total area:

$$A_{C60+}=\int A_{CNi} * dC_N, \text{ between } C_{60} \text{ and } C_{MAX}. \qquad \text{Eq. (11)}$$

Using Eq. (10) above and performing the integration, Eq. (11), provides the formula:

$$A_{C60+}=A_{C60} \times C_{Ni}-1261.9048(C_{Ni}^2/2-60C_{Ni}) \qquad \text{Eq. (12)}$$

Calculating $A_{C60+}$ with $C_{Ni}$ between 60 and $C_{MAX}$, provides $A_{C60}=2,504,249.92$.

There is a small difference between the $A_{C60+}$ of 2,504,249.92 calculated here and the $A_{C60+}$ of 2,484,979 calculated at Eq. (8) due to the rounding up of the $C_{MAX}$ to an integer, in this example from 122.52 to 123.

Using the $A_{Etotal}$ above from the gas chromatograph, the mass fraction of $C_{60+}$ ($MF_{C60+}$) may be determined:

$$MF_{C60+}=A_{C60+}/(A_{Etotal}+A_{NEC60+}) \qquad \text{Eq. (13)}$$

Using the $A_{C60+}$ calculated above, the $A_{Etotal}$ from the gas chromatograph, and using the $A_{NEC60+}=A_{EC60+}(R-1)$ from Eq. (1), the mass fraction of $C_{60+}$ is:

$$MF_{C60+}=A_{C60+}/(A_{Etotal}+A_{EC60+} \times (R-1)) \qquad \text{from Eq. (13)}$$

Using $A_{NEC60+}=A_{EC60+}(R-1)$ from equation (1), and the previously determined $A_{EC60+}$ and R, solving Eq. (13) provides:

$$MF_{C60+}=2,504,249.92/(14,290,000+1,908,000 \times (1.3024-1))$$

$$MF_{C60+}=0.1684 \qquad \text{from Eq. (13)}$$

This indicates that, in this example, the mass fraction for $C_{60+}$ is 0.168.

Molecular Weight

Figure 4A:
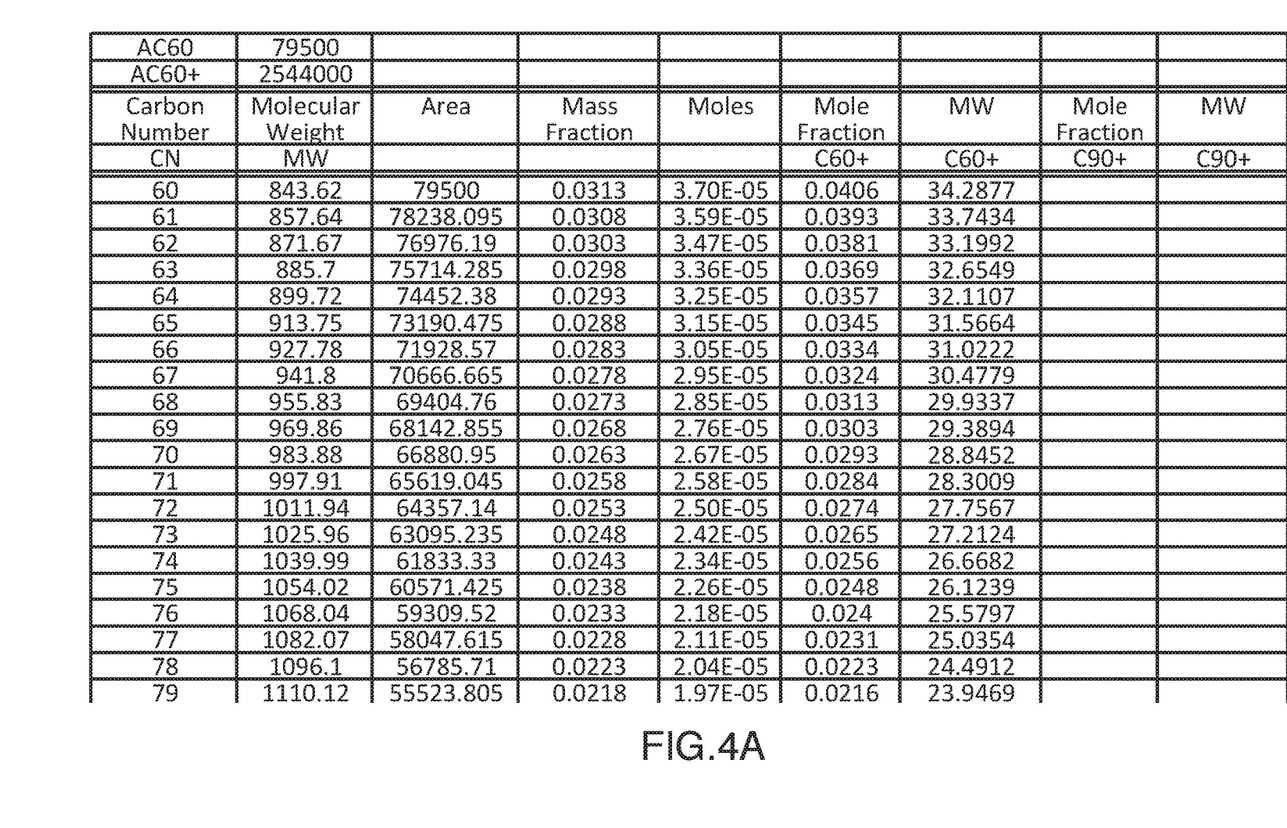
FIGS. 4A-4C is a table for an example of the present disclosure.
Figure 4B:
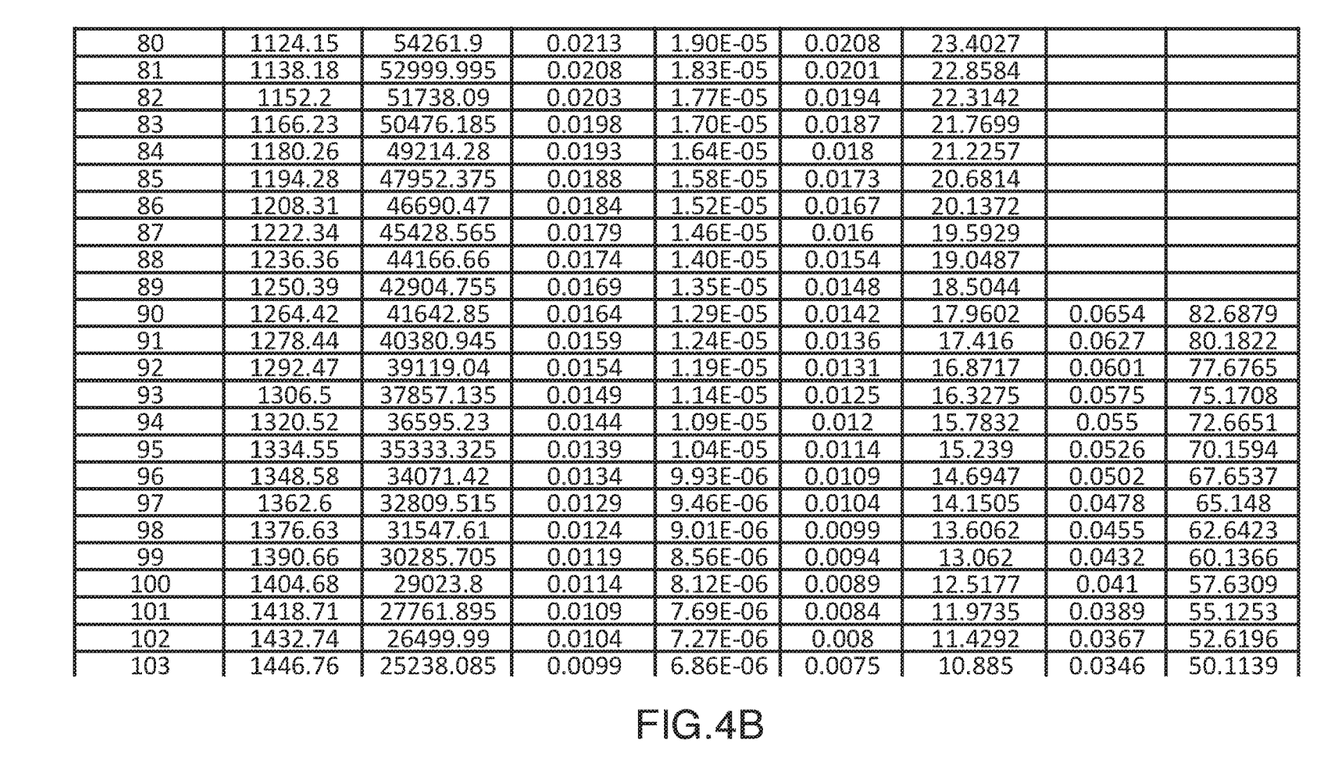
Figure 4C:
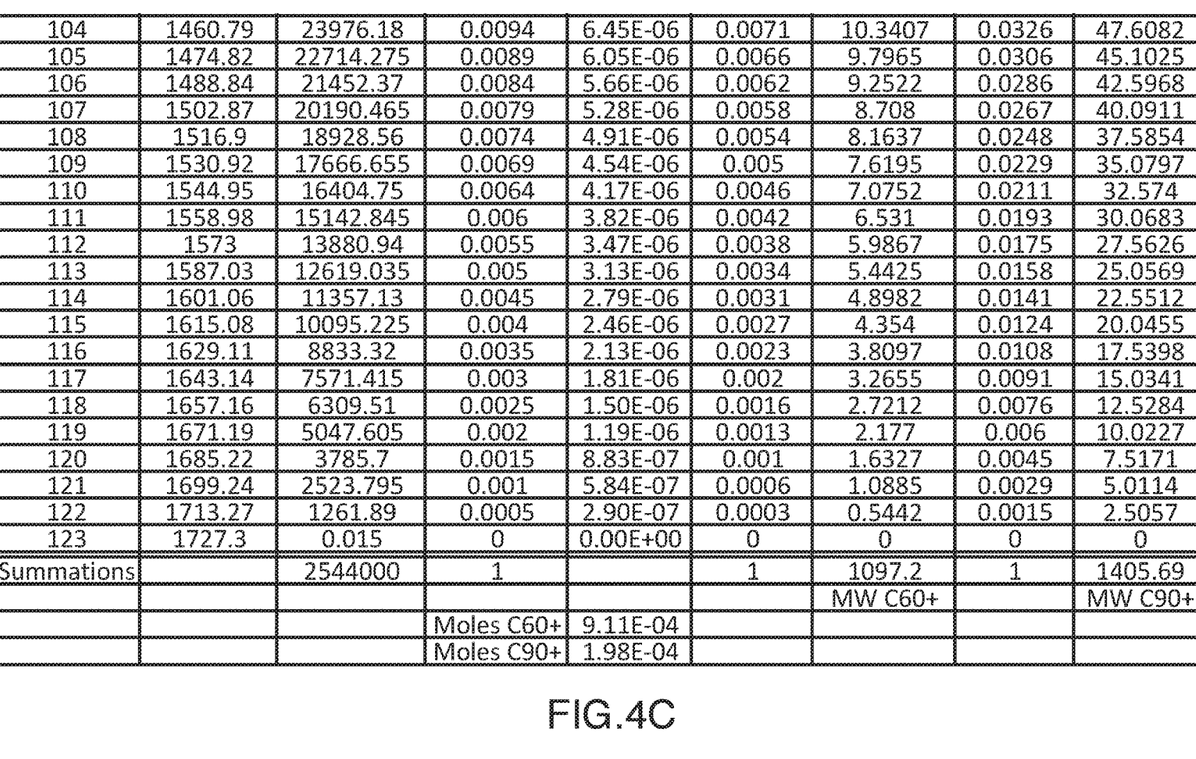

Referring to FIGS. 4A-4C, a table provides an example determination of the molecular weight $C_{60+}$ ($MW_{C60+}$) and molecular weight $C_{90+}$ ($MW_{C90+}$) using the methods described herein. Such quantifications are commonly used for calculations or analysis, for example computer simulations of heavy oil reservoirs.

For each carbon number, $C_{Ni}$, the molecular weight, area, mass fraction, moles, $C_{60+}$ mole fraction, and $C_{90+}$ mole fraction may be determined.

It is assumed that the hydrocarbon is an alkane, i.e. $C_nH_{2n+2}$. Using a molecular weight of C of 12.01078 g/mol and a molecular weight of H of 1.007947 g/mol, for example, $C_{100}$, as $C_{100}H_{202}$, would have a molecular weight of $100 \times 12.01078+202*1.007944=1,404.68$ g/mol.

The area for $C_{100}$, as $A_{C100}$ may also be calculated, as above, and as shown in FIGS. 4A-4C, $A_{C100}$ is 29,023.8.

The areas for each of $C_m$ may be totaled. In FIGS. 4A-4C, the total area for $C_{60}$ through $C_{123}$ is 2,504,250. Again, there is a small difference between the $A_{C60+}$ of 2,504,250 calculated here and the $A_{C60+}$ of 2,504,250 and the $A_{C60+}$ of 2,484,979 calculated earlier.

For each $C_{Ni}$, the mass fraction may be determined from the area divided by the total area. In the example, $C_{100}$, having an area $A_{C100}$ of 29,023.8 divided by the total area of 2,544,000 provides the mass fraction of $C_{100}$. As shown the mass fraction of $C_{100}$ is $29,023.8/2,544,000=0.0114$. The number of moles of $C_{100}$ is the mass fraction divided by the molecular weight, that is $0.0114/1,404.68.45=8.1219 \times 10^{-6}$. This is repeated for each $C_{Ni}$ between $C_{60}$ through $C_{MAX}$.

The number of moles for $C_{60+}$ and $C_{90+}$ may be summed. As shown in FIGS. 4A-4C, the total $C_{60+}$ is $9.114 \times 10^{-4}$ and the total for $C_{90+}$ is $1.9796 \times 10^{-4}$.

The mole fraction may be calculated for each $C_{Ni}$, for each of $C_{60+}$ and $C_{90+}$. As shown in the example in FIGS. 4A-4C, the mole fraction for $C_{100}$ is 0.0089 for $C_{60+}$ and 0.0410 for $C_{90+}$.

The mole fraction for each $C_{Ni}$ may be multiplied by the molecular weight, and the product sum provides the molecular weight. In the example shown in FIGS. 4A-4C, the molecular weight of the $C_{60+}$ components is 1,097.20 g/mol, and the molecular weight of the $C_{90+}$ components is 1,405.69 g/mol.

Total Oil

The composition of the whole oil may be provided using the complete elution of the $C_5$ to $C_{59}$ components from the gas chromatograph combined with the $C_{60+}$ as determined in accordance with the present disclosure.

General

The technique can easily be generalized to provide the molecular weight and mass fraction for a selected plus fraction.

As used herein, heavy oil is defined as petroleum liquids having an API gravity of less than about 12° API (i.e. a density of greater than 986 kg/m³).

In an alternative embodiment, the quantification may be made using another selected plus-fraction, for example $C_{90+}$ or another selected plus-fraction. As an example, another selected plus-fraction may be $C_{50+}$, $C_{120+}$ or $C_{100+}$ or some other selected plus-fraction, in which case the selected plus-fraction would be substituted in the above description for $C_{60+}$. That is, for example, the selected cutoff could be at other than $C_{60}$, with corresponding adjustments in the above method.

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art without departing from the scope, which is defined solely by the claims appended hereto.

What is claimed is:

1. A method of determining composition for a heavy oil, the method comprising:
    analyzing a sample of a heavy oil with a gas chromatograph to obtain analysis results for the heavy oil, comprising:
        running the sample of the heavy oil through a gas chromatograph column, the sample including an eluted portion and a plus fraction portion; and
        eluting the eluted portion from the gas chromatograph column;
    determining a highest detected carbon number ($C_{EMAX}$), a total eluted area ($A_{Etotal}$), and a $C_{60+}$ eluted area ($A_{EC60+}$) in the analysis results;
    setting an elution ratio (R) to compensate for non-elution of a plus-fraction of the heavy oil from the gas chromatograph according to a pre-established correlation between a ratio of the $C_{60+}$ eluted area ($A_{EC60+}$) to the total eluted area ($A_{Etotal}$) for heavy oil samples and the elution ratio (R);
    determining a corrected plus-fraction area ($A_{C60+}$) from the elution ratio (R) and the $C_{60+}$ eluted area ($A_{EC60+}$) according to the formula:

$A_{C60+} = A_{EC60+} \times R$; and determining a $C_{60}$ area ($A_{C60}$) and maximum carbon number ($C_{MAX}$) for the heavy oil according to the formulas:

$A_{EC60+} = 0.50 \times (C_{EMAX} - 60) \times A_{C60}$ and $A_{C60+} = 0.50 \times (C_{MAX} - 60) \times A_{C60}$.

2. The method of claim 1, wherein the pre-established correlation is the formula:

$R = 0.0493 \ln(A_{C60+}/A_{Etotal} \times 100) + 1.1746$.

3. The method of claim 2, further comprising:
    determining a slope of a non-elution line according to the formula:

$\text{slope} = (0 - A_{C60})/(C_{MAX} - 60)$; and determining at least one area fraction for a carbon number ($C_{Ni}$) according to the formula:

$A_{CNi} = A_{C60} + \text{slope} \times (C_{Ni} - 60)$.

4. The method of claim 3, further comprising determining an area fraction $A_{CNi}$ for each carbon number ($C_{Ni}$) between $C_{60}$ and $C_{MAX}$.

5. The method of claim 4, further comprising determining a mole fraction for each carbon number ($C_{Ni}$) between $C_{60}$ and $C_{MAX}$.

6. The method of claim 5, further comprising summing the molecular weight fraction for each carbon number ($C_{Ni}$) between $C_{60}$ and $C_{MAX}$ to determine a $C_{60+}$ molecular weight ($MW_{C60+}$) for the heavy oil.

7. The method of claim 5, further comprising summing the molecular weight fraction for each carbon number ($C_{Ni}$) between $C_{90}$ and $C_{MAX}$ to determine a $C_{90+}$ molecular weight ($MW_{C90+}$) for the heavy oil.

8. The method of claim 5, further comprising summing the molecular weight fraction for each carbon number ($C_{Ni}$) between $C_{MIN}$ and $C_{MAX}$ to determine a molecular weight (MW) for the heavy oil.

9. The method of claim 8, wherein $C_{MIN}$ equals $C_3$.

10. The method of claim 2, further comprising determining a plus-fraction area, between $C_{60}$ and $C_{MAX}$, according to the formula:

$A_{C60+} = \int A_{CNi} * dC_N$.

11. The method of claim 2, further comprising determining a plus-fraction area, between $C_{60}$ and $C_{MAX}$, according to the formula:

$A_{C60+} = A_{C60} \times C_{Ni} + \text{slope}(C_{Ni}^2/2 - 60 \times C_{Ni})$.

12. The method of claim 2, wherein $A_{C60+}/A_{Etotal} \times 100$ is between 1 percent and 100 percent.

13. The method of claim 12, wherein $A_{C60+}/A_{Etotal} \times 100$ is between 2 percent and 40 percent.

14. The method of claim 13, wherein $A_{C60+}/A_{Etotal} \times 100$ is between 2 percent and 30 percent.

15. A computer implemented method for determining composition for a heavy oil, the method comprising:
    obtaining gas chromatographic analysis results for a sample of a heavy oil, comprising:
        running the sample of the heavy oil through a gas chromatograph column, the sample including an eluted portion and a plus fraction portion; and
        eluting the eluted portion from the gas chromatograph column;
    determining a highest detected carbon number ($C_{EMAX}$), a total eluted area ($A_{Etotal}$), and a $C_{60+}$ eluted area ($A_{EC60+}$) in the gas chromatographic analysis results for the heavy oil;

setting an elution ratio (R) to compensate for non-elution of a plus-fraction of the heavy oil from a gas chromatograph used in obtaining the gas chromatographic analysis results according to a pre-established correlation between a ratio of the $C_{60+}$ eluted area ($A_{EC60+}$) to the total eluted area ($A_{Etotal}$) for heavy oil samples and the elution ratio;

determining a corrected plus-fraction area ($A_{C60+}$) from the elution ratio (R) and the $C_{60+}$ eluted area ($A_{EC60+}$) according to the formula:

$A_{C60+} = A_{EC60+} \times R$; and determining a $C_{60}$ area ($A_{C60}$) and maximum carbon number ($C_{MAX}$) for the heavy oil according to the formulas:

$A_{EC60+} = 0.50 \times (C_{EMAX} - 60) \times A_{C60}$ and $A_{C60+} = 0.50 \times (C_{MAX} - 60) \times A_{C60}$.

16. The method of claim 15, wherein the pre-established correlation is the formula:

$R = 0.0493 \ln(A_{C60+}/A_{Etotal} \times 100) + 1.1746$.

17. A non-transitory computer-readable medium having computer-readable code embodied therein, the computer-readable code executable by a processor of a computing device to implement a method for determining composition for a heavy oil, the implemented method comprising:
obtaining gas chromatographic analysis results for a sample of a heavy oil, comprising:
running the sample of the heavy oil through a gas chromatograph column, the sample including an eluted portion and a plus fraction portion; and
eluting the eluted portion from the gas chromatograph column;

determining a highest detected carbon number ($C_{EMAX}$), a total eluted area ($A_{Etotal}$), and a $C_{60+}$ eluted area ($A_{EC60+}$) in the gas chromatographic analysis results for the heavy oil;

setting an elution ratio (R) to compensate for non-elution of a plus-fraction of the heavy oil from a gas chromatograph used in obtaining the gas chromatographic analysis results according to a pre-established correlation between a ratio of the $C_{60+}$ eluted area ($A_{EC60+}$) to the total eluted area ($A_{Etotal}$) for heavy oil samples and the elution ratio (R);

determining a corrected plus-fraction area ($A_{C60+}$) from the elution ratio (R) and the $C_{60+}$ eluted area ($A_{EC60+}$) according to the formula:

$A_{C60+} = A_{EC60+} \times R$; and determining a $C_{60}$ area ($A_{C60}$) and maximum carbon number ($C_{MAX}$) for the heavy oil according to the formulas:

$A_{EC60+} = 0.50 \times (C_{EMAX} - 60) \times A_{C60}$ and $A_{C60+} = 0.50 \times (C_{MAX} - 60) \times A_{C60}$.

18. The non-transitory computer-readable medium of claim 17, wherein the pre-established correlation is the formula:

$R = 0.0493 \ln(A_{C60+}/A_{Etotal} \times 100) + 1.1746$.

* * * * *